United States Patent
Bundsgaard et al.

(10) Patent No.: US 11,657,600 B2
(45) Date of Patent: May 23, 2023

(54) METHOD FOR ASSESSING ORAL HEALTH USING A MOBILE DEVICE

(71) Applicant: Adent ApS, Copenhagen K (DK)

(72) Inventors: Richard Bundsgaard, Copenhagen K (DK); Thøger Bundsgaard, Copenhagen K (DK)

(73) Assignee: Adent ApS, Copenhagen K (DK)

( * ) Notice: Subject to any disclaimer, the term of this patent is extended or adjusted under 35 U.S.C. 154(b) by 0 days.

(21) Appl. No.: 17/765,795

(22) PCT Filed: Oct. 1, 2020

(86) PCT No.: PCT/EP2020/077547
§ 371 (c)(1),
(2) Date: Mar. 31, 2022

(87) PCT Pub. No.: WO2021/064114
PCT Pub. Date: Apr. 8, 2021

(65) Prior Publication Data
US 2022/0351500 A1    Nov. 3, 2022

(30) Foreign Application Priority Data
Oct. 4, 2019   (DK) .............................. PA201970623

(51) Int. Cl.
*G06V 10/776* (2022.01)
*G16H 50/30* (2018.01)
(Continued)

(52) U.S. Cl.
CPC .......... *G06V 10/776* (2022.01); *G06T 7/0012* (2013.01); *G06V 10/56* (2022.01);
(Continued)

(58) Field of Classification Search
CPC .. G06V 10/56; G06V 10/764; G06V 10/7715; G06V 10/776; G06V 10/7796;
(Continued)

(56) References Cited

U.S. PATENT DOCUMENTS

| 2016/0038092 A1 | 2/2016 | Golay |
| 2019/0026598 A1 | 1/2019 | Salah et al. |
| 2021/0398275 A1* | 12/2021 | Go ........................ G06T 7/0012 |

FOREIGN PATENT DOCUMENTS

| CN | 109330730 | 2/2019 |
| EP | 1905350 | 4/2008 |

(Continued)

OTHER PUBLICATIONS

Teeth4life, teeth4life advert, YouTube [online][video]. Apr. 7, 2019 [retrieved on Mar. 17, 2020]. Retrieved from https://www.youtube.com/watch?v=6UnLt3vPPeM.

(Continued)

*Primary Examiner* — Nay A Maung
*Assistant Examiner* — Jose M Torres
(74) *Attorney, Agent, or Firm* — Crockett & Crockett, PC; K. David Crockett, Esq.

(57) ABSTRACT

A method for remotely assessing oral health of a user of a mobile device by obtaining, using the mobile device (40), at least one digital image (1) of said user's (30) oral cavity (31) and additional non-image data (2) comprising anamnestic information about the user (30). The digital image (1) is processed both using a statistical object detection algorithm (20) to extract at least one local visual feature (3) corresponding to a medical finding related to a sub-region of said user's oral cavity (31); and also using a statistical image recognition algorithm (21) to extract at least one global classification label (4) corresponding to a medical finding related to said user's oral cavity (31) as a whole. An (Continued)

assessment (10) of the oral health of said user (30) is determined based on the local visual feature(s) (3), the global classification label(s) (4) and the non-image data (2).

13 Claims, 5 Drawing Sheets

(51) Int. Cl.
| | | |
|---|---|---|
| *G16H 30/40* | (2018.01) | |
| *G06V 10/56* | (2022.01) | |
| *G06V 10/77* | (2022.01) | |
| *G06V 10/778* | (2022.01) | |
| *G06V 10/82* | (2022.01) | |
| *G06V 10/764* | (2022.01) | |
| *G06T 7/00* | (2017.01) | |

(52) U.S. Cl.
CPC ........ *G06V 10/764* (2022.01); *G06V 10/7715* (2022.01); *G06V 10/7796* (2022.01); *G06V 10/82* (2022.01); *G16H 30/40* (2018.01); *G16H 50/30* (2018.01); *G06T 2207/30036* (2013.01); *G06V 2201/033* (2022.01)

(58) Field of Classification Search
CPC .............. G06V 10/82; G06V 2201/033; G06T 7/0012; G06T 2207/10024; G06T 2207/20081; G06T 2207/20084; G06T 2207/30036; G16H 30/40; G16H 50/20; G16H 50/30; A61B 5/0022; A61B 5/0077; A61B 5/0088; A61B 5/4547; A61B 5/4552; A61B 5/7267; A61B 5/7425; A61B 5/6898; A61C 19/04; G01J 3/508

See application file for complete search history.

(56) References Cited

FOREIGN PATENT DOCUMENTS

| | | |
|---|---|---|
| KR | 20100060787 | 6/2010 |
| WO | WO2018029276 | 2/2018 |
| WO | WO2018185501 | 10/2018 |

OTHER PUBLICATIONS

Tabatabaei, BA. Automatic detection of periodontitis using intra-oral images, (abstract) INSPEC [online]. 39th Annual International Conference of the IEEE Engineering in Medicine and Biology Society (EMBC), Jul. 11, 2017.

Rana, A. Automated segmentation of gingival diseases from oral images, (abstract) INSPEC [online]. IEEE Healthcare Innovations and Point of Care Technologies (HI-POCT), Nov. 2017.

International Search Report and Written Opinion dated Jan. 14, 2021 from IA PCT/EP2020/077547.

Anantharaman, et al., Utilizing Mask R-CNN for Detection and Segmentation of Oral Disease, 2018 IEEE International Conference on Bioinformatics and Biomedicine (BIBM), IEEE, Dec. 3, 2018, pp. 2197-2204.

Pingali, Personal Oral Health Advisor Using Multimodal Sensing and Machine Learning with Smartphones and Cloud Computing, 2019 IEEE International Conference on Cloud Computing in Emerging Markets (CCEM), IEEE, Sep. 19, 2019, pp. 17-24.

Rana, et al. Automated Segmentation of Gingival Diseases from Oral Images, 2017 IEEE Healthcare Innovations and Point of Care Technologies (HI_POCT), IEEE, Nov. 6, 2017, pp. 144-147.

\* cited by examiner

METHOD FOR ASSESSING ORAL HEALTH USING A MOBILE DEVICE

TECHNICAL FIELD

The present disclosure relates generally to the field of oral health, and more particularly to a method for assessing oral health using digital images and non-image data (such as text input) obtained using a mobile device with a camera to determine whether someone is a candidate for an oral treatment.

BACKGROUND

Oral health assessment is crucial for early intervention against and preventive treatment of oral health problems. However, many people do not receive proper oral health assessment, for several reasons. For example, they may live in rural areas far from a dental clinic and may, hence, not have access to oral health assessment, or they may not have the economic means to consult with a dental professional, let alone to pay for a potential treatment. Further, many people may be disinclined to spend time and money on an initial oral health assessment or on regular dental checkups if they are not experiencing any apparent oral health problem, despite the fact that, sometimes, people may unknowingly have symptoms of compromised oral health or unknowingly be at risk of developing an oral health problem. In other cases, people may be experiencing a certain oral health problem or symptoms of an oral disease but may decide to wait before consulting with a professional, hoping that the problem or symptoms will go away. All these example scenarios are problematic since early and proper oral health assessment allows for early intervention and preventive treatment, thus preventing or reducing the occurrence or progress of many oral problems and diseases.

Systems for remote oral health assessment, often referred to as teledentistry, exist. These systems typically provide real-time and offline dental care such as diagnosis, treatment planning, consultation, and follow-up through electronic transmission of clinical data among patients and dental professionals, e.g. using smartphones or other mobile devices. Some known remote oral health assessment systems involve transmission of e.g. dental images from the patient. For example, the patient may use the front camera of his/her smartphone for capturing a dental image and may transmit the captured image via e.g. a web-based application on the smartphone for remote clinical assessment. However, these transmitted images are most commonly assessed visually by a dental professional, with or without taking into account additional clinical data regarding the patient's clinical history from a local or remote database. This process is not only costly but also requires a lot of time to get results, which may cause serious health issues in case a medical condition is recognized too late. In similar fashion, early detection of oral health related medical conditions and providing actionable, easy-to-follow, personalized advice regarding such a condition can not only prevent the escalation of such conditions but save the patient a lot of money otherwise spent on expensive treatments.

Accordingly, there is a need for technologies that provide users with quick and cheap access to high quality, precise, remote oral health assessment based on the current state of their oral cavity and additional anamnestic information that the users can provide using existing tools, such as a mobile device that is connected to the Internet and comprises an input interface (e.g. touchscreen) and a camera, without requiring medical expertise or training.

There further exists a need for an efficient and reliable processing method which is also flexible enough so that it can process both image and non-image input provided by an untrained user on a low-cost mobile device and provide, as a result, an assessment of the oral health of the user.

Furthermore, the assessment must cover the most common conditions of the different regions of the oral cavity including both the teeth, the gums, and the lips.

The method should also allow for remote and timely feedback to be provided to the user, in particular to determine whether the user is a candidate for an oral treatment, to identify any regions of the oral cavity which require professional attention and actionable steps to take.

SUMMARY

It is an object to provide a method and corresponding computer program product and computer-based system that fulfills these needs and thereby overcomes or at least reduces the problems mentioned above. The foregoing and other objects are achieved by the features of the independent claims. Further implementation forms are apparent from the dependent claims, the description, and the figures.

According to a first aspect, there is provided a computer-implemented method for assessing oral health of a user of a mobile device to determine whether the user is a candidate for an oral treatment, the method comprising:

obtaining at least one digital image of the user's oral cavity using a camera of a mobile device;

obtaining non-image data associated with the user using the mobile device, the non-image data comprising anamnestic information about the user;

processing the at least one digital image using a statistical object detection algorithm executed on a processor of the mobile device or a processor of a remote server to calculate the likelihood of at least one local visual feature corresponding to a medical finding related to a sub-region of the user's oral cavity;

processing the at least one digital image using a statistical image recognition algorithm executed on a processor of the mobile device or a processor of a remote server to calculate the likelihood of at least one global classification label corresponding to a medical finding related to the user's oral cavity;

determining an assessment of the oral health of the user using a processor of the mobile device or a processor of a remote server based on the likelihood of the at least one local visual feature, the likelihood of the at least one global classification label and the non-image data; and displaying the assessment for the user on a display of the mobile device.

The method described can provide users with quick and cheap access to high quality, precise, remote oral health assessment. The assessment is based on the current state of their oral cavity and can further take into account medical history that the users can provide using a simple mobile device that is connected to the Internet and comprises an input interface (e.g. touchscreen) and a camera, without requiring medical expertise or training. The option of providing non-image data comprising anamnestic information about the user can enhance both efficiency and accuracy of the algorithm(s) used to determine the oral health assessment by limiting the scope of possible outcomes as well as guiding the algorithm(s) towards a more accurate and relevant result. Processing both digital image and non-image data using the described specific arrangement of different algorithms and synthesizing the statistical outputs into a cohesive assessment thus enables to more accurately and effectively determine whether the user is a candidate for an oral treatment than using any prior art methods.

The method can also allow for remote and timely feedback to be provided to the user, in particular to identify any regions of the oral cavity which require professional attention and actionable steps to take.

In a possible embodiment at least one image for each of a set of predefined priority views of the user's oral cavity is obtained.

In a possible embodiment the at least one digital image and the non-image data are processed locally on the mobile device, using at least one processor of the mobile device. In another possible embodiment, the at least one digital image and the non-image data are transmitted to a remote server and processed on the remote server.

In a possible embodiment the statistical image recognition algorithm uses a neural network model, more preferably a deep neural network model. In a further possible embodiment, the statistical image recognition algorithm uses a VGG architecture or variants of this architecture, such as a VGG16 architecture.

In a possible embodiment the assessment is determined locally on the mobile device using at least one processor of the mobile device. In a further possible embodiment, the assessment is determined a remote server based on the extracted data from the statistical algorithms and the non-image data, which may all be already on the remote server or can be transmitted thereon via a computer network. In a further possible embodiment, the assessment is transmitted from the remote server for displaying to the user on the display of the mobile device.

In a possible embodiment the assessment comprises at least one of an indication of a diagnosis, a referral to a dental professional, an estimate of the urgency of the oral health problem, or a recommendation for self-treatment. In a further possible embodiment, the assessment comprises determining whether the user is a candidate for an oral treatment.

In a preferred embodiment at least one of the statistical algorithms treat and/or simulate the data as nominal data, assuming an underlying unordered nature of discrete categories.

In another preferred embodiment at least one of the statistical algorithms treat and/or simulate the data as ordinal data, assuming an underlying ordered nature of discrete categories.

In a further possible embodiment at least one of the statistical algorithms treat and/or simulate the data as interval data, assuming an underlying comparable-distanced and ordered nature of non-discrete categories.

In a further possible embodiment at least one of the statistical algorithms treat and/or simulate the data as ratio data, assuming an underlying comparable-distanced, ordered nature of non-discrete categories with an "absolute zero" (corresponding to the total absence of a global classification and/or local feature).

In a possible implementation form of the first aspect, the at least one digital image is at least one of an intraoral or extraoral high resolution color photograph, preferably in the RGB or RGBA color space; and the method further comprises extracting at least one image derivative from the digital image by at least one of:

processing the at least one digital image to generate at least one scaled image by scaling the at least one digital image to optimal dimensions;

processing the at least one digital image to extract at least one image patch, each image patch comprising visual information of at least one tooth and its surrounding region within the oral cavity; and processing the at least one digital image to extract at least one image vector, each image vector representing the digital image in a reduced vector space; wherein processing the at least one digital image using a statistical algorithm comprises feeding the at least one image derivative to a version of the statistical algorithm optimized for the respective image derivative input; and wherein any classification resulting from feeding the at least one image patch to a statistical image recognition algorithm optimized for image patch input can correspond to at least one of a global classification label, or a local visual feature linked to the respective at least one tooth and its surrounding region within the user's oral cavity.

In a further possible implementation form of the first aspect the non-image data comprises self-reported user input obtained using the mobile device in the form of at least one of a checklist, a slider bar, or free text; and the method further comprises:

processing the non-image data using a syntax analysis algorithm to extract a structured database of non-image signals, the non-image signals indicating at least one of
symptoms or signs of health regarding intraoral colors, surface structures, contours, wounds, texture, general health, taste in mouth, breath, saliva, healing process, pain;
symptom triggers related to touch or icing, biting down, movement of tongue or jaw; or
behavioral data regarding oral habits, general health, medicine intake, comorbidities of periodontitis, history of trauma, history of oral procedures, pregnancy, or tobacco usage.

In a further possible implementation form of the first aspect processing the at least one digital image using a statistical object detection algorithm arranged to calculate the likelihood of at least one local visual feature comprises: feeding the at least one digital image or at least one of its image derivatives to at least one classification algorithm arranged to predict each of the at least one local visual feature independently, wherein the at least one classification algorithm is arranged to further predict:
the likelihood of the respective local visual feature, and
at least one local reference indicating a location corresponding to the respective local visual feature on the digital image or any of its image derivatives.

In a possible embodiment the statistical object detection algorithm comprises individual binary algorithms optimized for each of the at least one local visual feature respectively, arranged to further predict the likelihood of the local visual feature, a pointer (such as a boundary box, circle, or point) indicating the location of the local visual feature, and/or an object mask for the local visual feature.

In a further possible implementation form of the first aspect the statistical object detection algorithm uses a neural network model, more preferably a convolutional neural network model. In a possible embodiment the statistical object detection algorithm uses an R-CNN model or variants of this architecture. In a further possible embodiment, the statistical object detection algorithm uses a Faster RCNN model or variants of this architecture. In a further possible embodiment, the statistical object detection algorithm uses a Mask R-CNN model or variants of this architecture. In a further possible embodiment, the statistical object detection algorithm uses ResNet or variants of this architecture. In a further possible embodiment, the statistical object detection algorithm uses a YOLO (You Only Look Once) model or variants of this architecture.

In a further possible implementation form of the first aspect the method further comprises:

processing the non-image data or its derivative database of non-image signals, and the at least one local visual feature using a statistical or non-statistical algorithm arranged to extract a set of priority classification labels corresponding to a predefined number of prioritized medical findings of the user's oral cavity, and relative likelihoods of the priority classification labels based on predefined conditions;

arranging the set of priority classification labels into a subset of priority classification labels of highest relative likelihoods; and using the subset of priority classification labels as further input for at least one of the statistical object detection algorithm or the statistical image recognition algorithm to enhance the predictability of the at least one local visual feature or the at least one global classification label.

In a possible embodiment the non-image data or its derivative database of non-image signals, and the at least one local visual feature is processed using filtered queries on a reference database, wherein the reference database may comprise a multi-dimensional set of conditionals, such as age, gender, body structure, and various symptom types, branching into a plurality of dental concepts.

In a further possible implementation form of the first aspect the method further comprises:

processing the at least one digital image or at least one of its image derivatives using a second statistical image recognition algorithm arranged to predict a set of pre-classification labels corresponding to the most likely possible medical findings of the user's oral cavity; and using the set of pre-classification labels as input condition for at least one of the statistical object detection algorithm or the statistical image recognition algorithm to limit the possible result pool of either or both of the algorithms.

In a possible embodiment the second statistical image recognition algorithm uses a neural network model, more preferably a deep neural network model. In a further possible embodiment, the second statistical image recognition algorithm uses a VGG architecture or variants of this architecture, such as a VGG16 architecture.

In a further possible implementation form of the first aspect at least one of:

the at least one local visual feature is used as further input for the statistical image recognition algorithm to enhance the predictability of the at least one global classification label; or the at least one global classification label is used as further input for the statistical object detection algorithm to enhance the predictability of the at least one local visual feature.

In a further possible implementation form of the first aspect the at least one global classification label corresponds to at least one of "gingivitis", "periodontitis", "dental cavities", or "herpes labialis".

In a further possible implementation form of the first aspect one or more predefined local visual feature may increase the likelihood of at least one global classification label, such as:

"swelling gums", "bleeding gums", "redness of gums", "dental plaque" may increase the likelihood of "gingivitis";

"exposure of root", "abrasion of tooth", "staining of tooth", "recession of gums" may increase the likelihood of "periodontitis";

"white spot lesion", "brown/black discoloration of tooth", "enamel breakdown", "shade on enamel", "dental plaque" may increase the likelihood of "dental cavities"; and "inflamed papules and vesicles", "fluid-filled blister", "local redness of lip", "open ulcer" may increase the likelihood of "herpes labialis".

In a further possible implementation form of the first aspect determining the assessment of the oral health of the user comprises:

feeding the likelihood of the at least one local visual feature, optionally together with its at least one local reference, and the likelihood of the at least one global classification label to a synthesizing algorithm arranged to map local visual features to global classification labels and to determine a set of concepts, each concept comprising at least one global classification label and any number of related local visual features and their optional local references; and validating the set of concepts either automatically or by a human dental reviewer based on medical certainty, wherein the medical certainty is determined based on at least one of:

predefined threshold values for the likelihoods of the global classification labels and related local visual features comprised in each concept; and predefined threshold values for validity scores associated with each statistical algorithm used for predicting the likelihoods.

In a further possible implementation form of the first aspect the method further comprises:

processing the list of concepts using a specialist reference database and flagging any concept comprising a classification label or a related local visual feature that is defined in the specialist reference database as any one of extraordinarily rare, extraordinarily malignant, or transcending into the domain of general health; and if a concept is flagged, forwarding it to a human specialist dental reviewer for validation;

if medical certainty of a concept is lower than a predefined medical certainty threshold but the concept is not flagged, forwarding it to a human general dental reviewer for validation; and validating the remaining list of concepts using a validation algorithm arranged for automatic concept validation based on a predefined set of validation rules.

In an embodiment the role of human general dental reviewer is filled by the same person as the human specialist dental reviewer.

In a further possible implementation form of the first aspect the method further comprises:

processing the list of validated concepts to determine additional components for the assessment, the additional components comprising comments or prompts and possible or typical actions to take in case of an identified concept, global classification label or related local visual feature, wherein determining the additional components comprises at least one of:

determining a predefined component from multiple possible predefined components automatically based on predefined rules, editing a predefined component manually by a human reviewer, editing a predefined component automatically using a statistical natural language processing algorithm, determining a non-predefined component manually by a human reviewer, and determining a non-predefined component automatically using a statistical natural language processing algorithm; and determining an assessment of the oral health of the user based on the validated list of concepts and the additional components.

In a possible embodiment the list of validated concepts is processed using a parsing algorithm arranged to parse through each validated concept and extract comments and actions from database comprising predefined comments or prompts and possible/typical actions to take given a noted issue. In an embodiment the database is based on research-based dental knowledge on typical visual signs, actions, and suggestions on behavioral adjustments related to concepts combined with personalized documentation for the user.

In a possible embodiment, the method further comprises validating said full assessment either automatically or by the general or specialist dental reviewer based on medical certainty and the presence of any flagged concept. In a further possible embodiment, the method further comprises filtering said full assessment using a filter database to mask, remove or replace any concept defined as sensitive in said filter database, such as a "malignant tumor".

According to a second aspect, there is provided a computer program product, encoded on a computer-readable storage medium, operable to cause a processor to perform operations according to any possible implementation form of the first aspect.

According to a third aspect, there is provided a system for assessing oral health of a user, the system comprising: a mobile device comprising a camera for obtaining at least one digital image of the user's oral cavity;

a machine-readable storage medium comprising a program product; and one or more processors operable to execute the program product and perform operations according to any possible implementation form of the first aspect.

These and other aspects will be apparent from and the embodiment(s) described below.

BRIEF DESCRIPTION OF THE DRAWINGS

In the following detailed portion of the present disclosure, the aspects, embodiments, and implementations will be explained in more detail with reference to the example embodiments shown in the drawings, in which.

DETAILED DESCRIPTION

Figure 1:
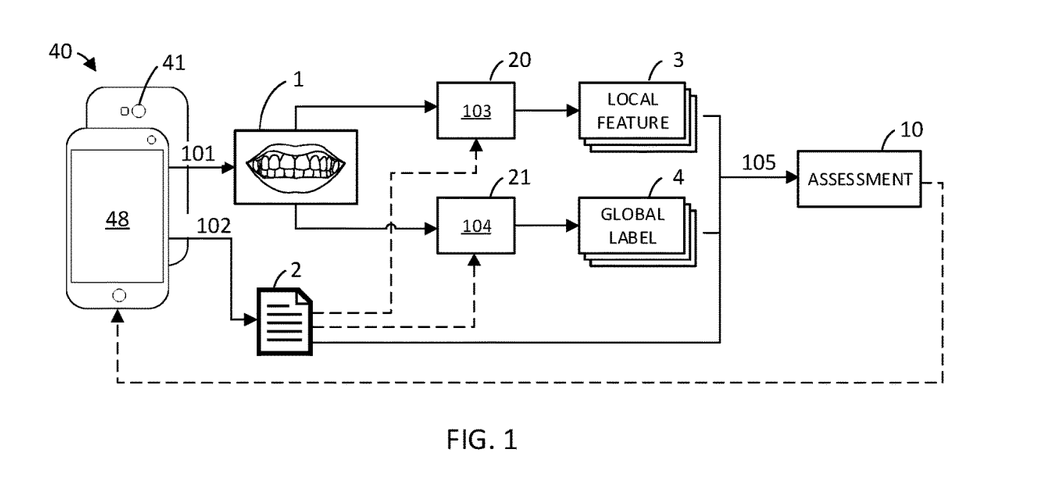
FIG. 1 shows a flow diagram of a method for assessing oral health of a user in accordance with the first aspect, using a system in accordance with the third aspect.
Figure 11:
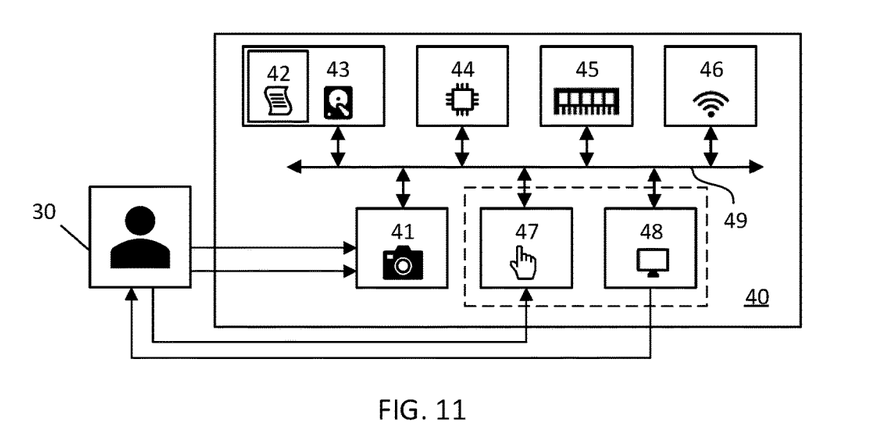
FIG. 11 is a block diagram of a system for assessing oral health of a user in accordance with a possible implementation form of the second aspect.

FIG. 1 shows a flow diagram of a method for assessing oral health of a user of a mobile device in accordance with the present disclosure, using a computer-based system such as for example the system shown on FIG. 11.

A mobile device 40 is provided, as part of the computer-based system, comprising at least one camera 41 configured to capture digital images and means for obtaining further non-image input. The mobile device 40 is a portable computing device. In the embodiment illustrated in FIG. 1, the mobile device 40 is a smartphone, comprising both a front camera above the display 48 and a main camera 41 on the rear side. In another embodiment, the mobile device 40 may be e.g. a tablet computer (tablet) with corresponding features (display and camera).

In an embodiment, the mobile device 40 is configured to execute an application software ("app") and comprises a camera 41 for capturing images and a display 48 for displaying the images (as part of a user interface), wherein the display 48 and the camera 41 are provided on opposite sides of the housing of the mobile device 40. In another embodiment, the camera 41 for capturing images may be a secondary camera provided on the same side of the housing of the mobile device as the display 48. In an embodiment the display 48 may comprise a touch screen that provides the means for obtaining non-image input from the user by user interaction with the help of a graphical user interface (GUI).

In an initial step 101, at least one digital image 1 of the oral cavity 31 of the user 30 of the mobile device 40 is obtained using a camera 41 of the mobile device 40.

Herein, "oral cavity" may refer to e.g. lips, hard palate, soft palate, retromolar trigone (area behind the wisdom teeth), tongue, gingiva (gums), buccal mucosa, the floor of the mouth under the tongue, and/or teeth.

The user 30 may capture the digital image(s) 1 with the camera 41 of the mobile device 40 and/or may add existing images from a gallery available e.g. on or via the mobile device 40 that were taken with the camera 41 beforehand. The obtained digital image(s) 1 may be both an intraoral or extraoral high resolution color photograph(s), preferably in the RGB or RGBA color space.

For providing the at least one digital image, the user 30 may be prompted to select a particular view/pose annotation describing the view/pose of the images, e.g. closed mouth view, bite view, bottom/lower arch view, upper arch view, bottom/lower lip view, upper lip view, closed bite anterior view, open bite anterior view, closed bite buccal view, open bite buccal view, roof of mouth view, floor of mouth view, side of mouth view, or frontal view, and may be guided to capture an image in the selected particular view/pose. In an embodiment the user 30 may be required to provide at least one image for each of a set of predefined priority views, such as a 'frontal view with closed bite', a 'bottom lip pulled down, exposing teeth in lower mouth and the inner bottom lip' and 'top lip pulled up, exposing teeth in top mouth and the inner top lip'.

In an embodiment, the person whose oral cavity is captured on image is the same person as the person operating the mobile device 40 for obtaining the one or more digital images 1. In another embodiment, the person operating the mobile device 40 is not the same person as the person whose oral cavity is captured on image. This may, for example, be the case when the person whose oral cavity is captured on image is a child or other person requiring help, e.g. from a parent or other family member, for capturing the one or more images of an area of his/her oral cavity.

As a further step 102, non-image data 2 associated with the user 30 is also obtained using the mobile device 40. The non-image data 2 comprises anamnestic information about the user 30, wherein "anamnestic information" may refer to any type of information regarding the patient's medical history as well as any current symptoms (see described below in detail). Herein, the numbering of steps does not correspond to a strict order of execution—obtaining the non-image data 2 can happen in the same time, before and/or after obtaining the digital image(s) 1.

In an embodiment the non-image data 2 comprises self-reported user input given by the user via e.g. a touchscreen interface of the mobile device 40. In an embodiment the input may be obtained in the form of a dialogue, where the user 30 answers an automatically generated or predefined sequence of questions and the answers are recorded on the mobile device 40. In an embodiment the questions may be received, and the answers may be given in the form of a checklist, a slider bar, a visual representation, and/or free text through a touchscreen, or as spoken text. In an embodiment, a 3D representation of an oral cavity may be presented to the user 30 for indicating in the representation an area corresponding to the area of the user's own oral cavity associated with an oral health problem. The area may e.g. be a specific tooth. The user's answers may be finite answers. For example, the user 30 may select one or more suggestions from a checklist. In an embodiment the sequence of questions to the user 30 may comprise questions relating to past and present behavioral data (such as tobacco use and oral hygiene habits), symptoms, symptom triggers, and/or temporal contextual variables such as urgency. In an embodiment the symptoms may be symptoms of at least one of gingivitis, periodontitis, dental caries, abrasion of tooth, bruxism, cold sore, erosion of teeth, fluorosis, herpes labialis, herpes zoster, or herpes infection.

In a preferred embodiment, the user is presented with a text-based dialogue on the display 48 of the mobile device 40, the dialogue comprising a sequence of questions arranged to guide the user through a process of combined input of both non-image data 2 and digital image(s) 1 in one flow.

Once obtained, both the non-image data 2 and the digital image(s) are processed using a dedicated arrangement of statistical algorithms for extracting classifications relating to both at least one sub-region of the user's oral cavity 31, and to the oral cavity 31 as a whole. Herein, "classification" may refer to a classification on nominal, ordinal, interval, and/or ratio data. Each form represents different modes of collecting data on oral health. The preferred output assumes a global classification and/or a local feature including an associated score and/or positional reference, but given the underlying distribution of oral health.

A preferred embodiment includes using statistical algorithms that treat and/or simulate the data as nominal data, assuming an underlying unordered nature of discrete categories. Another preferred embodiment includes using statistical algorithms that treat and/or simulate the data as ordinal data, assuming an underlying ordered nature of discrete categories.

A further possible embodiment includes using statistical algorithms that treat and/or simulate the data as interval data, assuming an underlying comparable-distanced and ordered nature of non-discrete categories.

A further possible embodiment includes using statistical algorithms that treat and/or simulate the data as ratio data, assuming an underlying comparable-distanced, ordered nature of non-discrete categories with an "absolute zero" (corresponding to the total absence of a global classification and/or local feature).

Figure 12:
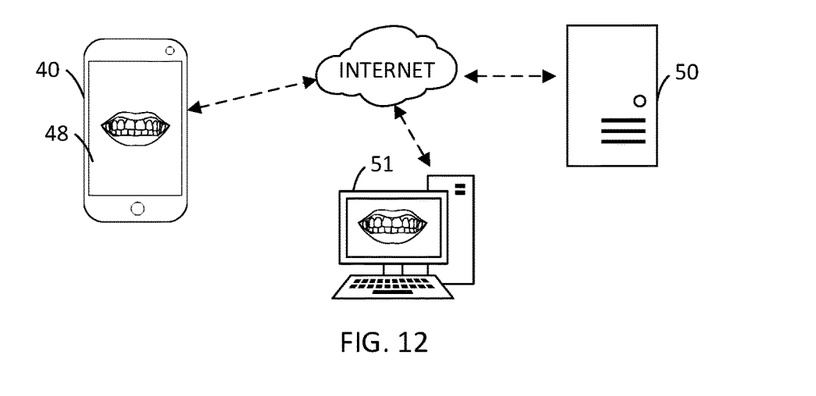
FIG. 12 is a diagrammatic representation of a wireless system in accordance with a possible implementation form of the second aspect.

In an embodiment the at least one digital image 1 and the non-image data 2 are processed locally on the mobile device 40, using at least one processor 44 of the mobile device 40. In another embodiment the at least one digital image 1 and the non-image data 2 are transmitted, using a computer network, to a remote server 50 as shown in FIG. 12, and processed remotely on the server 50.

The at least one digital image 1 is then processed 103 using a statistical object detection algorithm 20 that is trained for predicting local visual features 3 and their likelihood scores.

In an embodiment the statistical object detection algorithm uses a neural network model, more preferably a convolutional neural network (CNN) model.

In an embodiment the statistical object detection algorithm 20 may use an R-CNN model (and variants of this architecture), wherein the "R" refers to any extracted local feature 3 being associated with a Region (sub-region) of the input image 1. In an R-CNN model the CNN is forced to focus on a single region of the input image 1 at a time to minimize interference. Thus, it is expected that only a single object of interest will dominate in a given region. The regions in the R-CNN are detected by selective search algorithm followed by resizing, so that the regions are of equal size before they are fed to a CNN for classification and bounding box regression. The output of this model is thus at least one local visual feature 3 with a corresponding bounding box and likelihood.

In a possible embodiment, the statistical object detection algorithm 20 may use a Faster RCNN model (and variants of this architecture) for bounding box object detection of local visual features 3 as described above. While the above algorithms (R-CNN, and even its faster implementation Fast R-CNN) use selective search to find out the region proposals, which is a slow and time-consuming process affecting the performance of the network, the Faster RCNN model is an object detection algorithm that eliminates the selective search algorithm and lets the network learn the region proposals. Similar to R-CNN (or Fast R-CNN), the digital image 1 is provided as an input to a convolutional network which provides a convolutional feature map. However, instead of using selective search algorithm on the feature map to identify the region proposals, a separate network is used to predict the region proposals. The predicted region proposals are then reshaped using a RoI (Region of Interest) pooling layer which is then used to classify the image within the proposed region and predict the offset values for the bounding boxes.

In another possible embodiment, the statistical object detection algorithm 20 may (also) use a Mask R-CNN model, which extends the R-CNN model by adding a branch for predicting an object mask in parallel with the existing branch for bounding box recognition. In effect, the processing with a Mask-RCNN model has two stages. The first stage proposes candidate object bounding boxes, while the second stage extracts features using RoI (Region of Interest) Pooling from each candidate box and performs classification, and bounding box/mask regression. The output of this model is thus at least one local visual feature 3 with a corresponding bounding box, object mask and likelihood.

In another possible embodiment, the statistical object detection algorithm 20 may (also) use a ResNet (and variants of this architecture), for mask object detection of local visual features 3 as described above. The output of this model (or combination of models) is thus at least one local visual feature 3 with a corresponding bounding box, object mask and likelihood.

In another possible embodiment, the statistical object detection algorithm 20 may use a YOLO (You Only Look Once) model (and variants of this architecture) for bounding box object detection of local visual features 3 as described above. YOLO is an object detection algorithm much different from the region-based algorithms described above. In YOLO a single convolutional network predicts the bounding boxes and the class probabilities for these boxes. The output of this model is thus at least one local visual feature 3 with a corresponding bounding box and likelihood.

In an embodiment the statistical object detection algorithm 20 comprises individual binary algorithms optimized for each of the at least one local visual feature 3 respectively, arranged to further predict the likelihood of the local visual feature 3, a pointer (such as a boundary box, circle, or point) indicating the location of the local visual feature 3, and/or an object mask for the local visual feature 3.

In addition to, and as a pre-processing step before the above described deep learning algorithms, a number of feature-engineered algorithms may also be used for benchmarking and for amplifying performance in initial phases of introducing newly identified local visual features 3 by extracting and feeding as input to the deep learning network a set of further technical features, such as Histogram of Oriented Gradients (HOG) and/or ORB (a fusion of feature algorithms FAST and BRIEF).

The extracted local visual features 3 each correspond to a medical finding related to a sub-region of the user's oral cavity 31. Herein, a "medical finding" may refer to both normal and abnormal medical states, and a "sub-region" may refer to e.g. a single tooth, a gum area near a tooth, or a portion of one of the lips.

The extracted local visual features 3 can overall be categorized within (complimentary, and not mutually excluding):
 1. Form, contour, shape
 2. Color, gradient, shade
 3. Texture, surface, roughness A local visual feature 3 can be identified through a variety of different annotations, depending on the feature. Annotation types include boundary boxes, polygons, focal points, and individual labelling of intelligently identified subset/local patches of the entire image.

Some examples of local visual features 3 related to indications of gum disease or inflammation:
 Swelling of gums/type of feature: form, contour, shape
 Redness of gums/type of feature: color, gradient, shade
 Gradient of redness/type of feature: color, gradient, shade
 Bleeding gums
 Discolorations of teeth (due to lacking oral hygiene)/type of feature: color, gradient, shade
 External matter on teeth (due to lacking oral hygiene)/type of feature: texture, surface, roughness
 Presence of plaque
 Exposure of root/type of feature: (primarily) color, gradient, shade
 Recession of gums/type of feature: form, contour, shape
 Cliff separating enamel and dental/type of feature: Form, contour, shape The at least one digital image 1 is also processed 104 using a statistical image recognition algorithm 21 that is trained for predicting global classification labels 4 and their likelihood scores.

In an embodiment, the statistical image recognition algorithm 21 uses a neural network model, more preferably a deep neural network model.

In a possible embodiment, the statistical image recognition algorithm 21 uses a VGG architecture, which refers to a very deep neural network that uses little preprocessing of input images, and stacks of convolutional layers, followed by Fully Connected (FC) layers. The convolutional layers in the VGG architecture use filters with a very small receptive field and are therefore optimal for the processing of digital intraoral and extraoral images 1. The output of this model is thus at least global classification label 4 with a corresponding likelihood value.

In a further possible embodiment, the statistical image recognition algorithm 21 uses a VGG16 architecture, wherein "16" refers to the number of layers in the architecture. The extracted global classification labels 4 each correspond to a medical finding related to the user's oral cavity 31 as a whole. Herein, similarly as already defined above, a "medical finding" may refer to both normal and abnormal medical states. In an embodiment the at least one global classification label 4 corresponds to at least one of "gingivitis" (an inflammatory state of the gums), "active periodontitis" (an inflammatory state of the gums but at a later stage where the gums are detaching from the tooth/dentin), "inactive periodontitis" (a stable, non-inflammatory state of the gums after having long-term/persistent inflammation of the gums that is now under control, i.e. the gums have retracted chronically), "dental cavities" or "caries" (the decay of the tooth, i.e. the bone structure), and/or "herpes labialis" (a type of infection by the herpes simplex virus that affects primarily the lip, also known as "cold sores").

In a possible embodiment, at least one local visual feature is used as further input for the statistical image recognition algorithm 21 to enhance the predictability of the at least one global classification label 4.

In a further possible embodiment, the at least one global classification label 4 is used as further input for the statistical object detection algorithm 20 to enhance the predictability of the at least one local visual feature 3. In a further embodiment, one or more predefined local visual feature 3 may increase the likelihood of at least one global classification label 4.

In an embodiment, "swelling gums", "bleeding gums", "redness of gums", "dental plaque" may increase the likelihood of "gingivitis". In a further embodiment, "exposure of root", "abrasion of tooth", "staining of tooth", "recession of gums" may increase the likelihood of "periodontitis". In a further embodiment, "white spot lesion", "brown/black discoloration of tooth", "enamel breakdown", "shade on enamel", "dental plaque" may increase the likelihood of "dental cavities". In a further embodiment, "inflamed papules and vesicles", "fluid-filled blister", "local redness of lip", "open ulcer" may increase the likelihood of "herpes labialis".

In a further embodiment, "light coral pink gums", "stippled surface gums", "tightly fitting gumline on tooth" may increase the likelihood of "healthy gums".

In a final step, an assessment 10 of the oral health of the user 30 is determined based on the likelihood of the at least one local visual feature 3, the likelihood of the at least one global classification label 4 and the non-image data 2. Similarly as described above with respect to processing the at least one digital image 1 and the non-image data 2, in an embodiment the assessment 10 can be determined locally on the mobile device 40 using at least one processor 44 of the mobile device 40.

Similarly, in another possible embodiment the assessment 10 can also be determined a remote server 50 based on the extracted data from the statistical algorithms (the at least one local visual feature 3 with its corresponding likelihood, bounding box, and/or object mask, as well as the at least one global classification label 4 with its corresponding likelihood) and the non-image data 2, which may all be already on the server 50 or can be transmitted thereon using a computer network as shown in FIG. 12. The assessment 10 can then be transmitted for displaying to the user 30 on the display 48 of the mobile device 40.

Herein, "assessment" preferably refers to an assessment performed in order to determine the user's oral health condition. For example, the assessment may comprise at least one of monitoring the user's oral health condition, identifying any oral health problems, diagnosing any oral health diseases, identifying any oral health risks, or determining that no symptoms of any oral health problems or diseases are present. The user 30 may have observed symptoms of an oral health problem or disease and may therefore wish to obtain images of an area of his/her oral cavity 31 to have his/her oral health assessed based on the images. Or, the user 30 may not have observed any symptoms but may, nevertheless, wish to obtain images of an area of his/her oral cavity 31 to have his/her oral health assessed. In an embodiment, the assessment may be part of a dental health treatment or follow-up plan prescribed by a dental professional.

The assessment, whether performed locally or remotely, may comprise an indication of a diagnosis (i.e. identifying a risk of a disease or other oral health problem), a referral to a dental professional, an estimate of the urgency of the oral health problem, a recommendation for self-treatment, etc. Particularly, the oral health assessment, performed locally and/or remotely, may comprise determining whether the user 30 is a candidate for an oral treatment, e.g. dental treatment or treatment of cold sores on the lips, based on the images and informing the user 30 on the mobile device 40, preferably via an app, whether he/she is a candidate for an oral treatment.

Further, herein, "oral health problem" or "oral disease" may refer to at least one of Abnormal taste in mouth, Abrasion of tooth, Acid reflux, Acute necrotizing ulcerative gingivitis, Addison's disease, Alveolitis of jaw, Amalgam tattoo, Amelogenesis imperfecta, Anemia, Aphthous ulcer of mouth, Atrophy of tongue papillae, Black hairy tongue, Bleeding gums, Broken tooth injury, Bruxism (teeth grinding), Burning mouth syndrome, Cancer, Candidiasis, Cheek biting, Cheilosis, Chemical burn (mouth), Chicken pox (Varicella), Cold sore, Complete avulsion of tooth, Contusion, Crazing of enamel, Cyst, Dental caries, Dental filling lost, Dental peri-implant mucositis, Dental plaque, Dental restoration present, Dentinogenesis imperfecta, Denture stomatitis, Diastema of teeth, Early tooth exfoliation, Electrical burn, Enamel hypoplasia, Enlarged labial frenulum, Erosion of teeth, Eruption cyst, Erythema, Erythroleukoplakia of internal part of mouth, Excessive salivation, Fibroma, Fistula, Fluorosis, Fordyce's disease, Fracture of tooth, Fractured dental restoration, Geographic tongue, Gingival recession, Gingivitis, Glossopyrosis, Hemangioma, Herpes labialis, Herpes zoster, Herpes infection, Hyperplasia of gingiva, Infectious mononucleosis, Leukemia, Leukoedema, Leukoplakia, Lichen planus (mouth), Linea alba of oral mucosa, Lip biting, Lipoma, Lymphadenopathy, Malignant melanoma, Malignant tumor of major salivary gland, Malocclusion of teeth, Measles, Melanin pigmentation (mouth), Melanocytic nevus (mouth), Melanoma in situ (mouth), Mucocele of mouth, Mumps, Necrosis of the pulp, Osteoporosis, Pain in throat, Papillary hyperplasia, Papilloma, Parulis, Pemphigoid, Pemphigus, Pericoronitis, Periodontal abscess, Periodontitis, Pseudomembranous thrush, Pulpitis, Pyogenic granuloma, Rubella, Sexually transmitted infectious disease, Sialolithiasis, Sinusitis, Smokeless tobacco keratoses, Smoker's melanosis, Staining of tooth, Stomatitis, Subluxation of tooth, Syphilis, Teething syndrome, Temporomandibular joint disorder, Thermal burn, Tongue biting, Tonsillitis, Tooth absent, Tooth sensitivity to brush or floss, Tooth sensitivity to cold, Tooth sensitivity to palpation, Traumatic granuloma, Traumatic injury, Trigeminal neuralgia, Turner's Tooth, Ulcer, Verrucous carcinoma, Vitamin deficiency, Wegener's granulomatosis, White sponge nevus of mucosa, or Xerostomia. Further, herein, "oral health" or "oral health sign" may refer to at least one of Healthy gums, Healthy enamel, Healthy mucosa, Healthy tongue, Healthy lips, Healthy Roof of Mouth, Healthy Saliva Gland, or the absence of any oral health problem.

Figure 2:
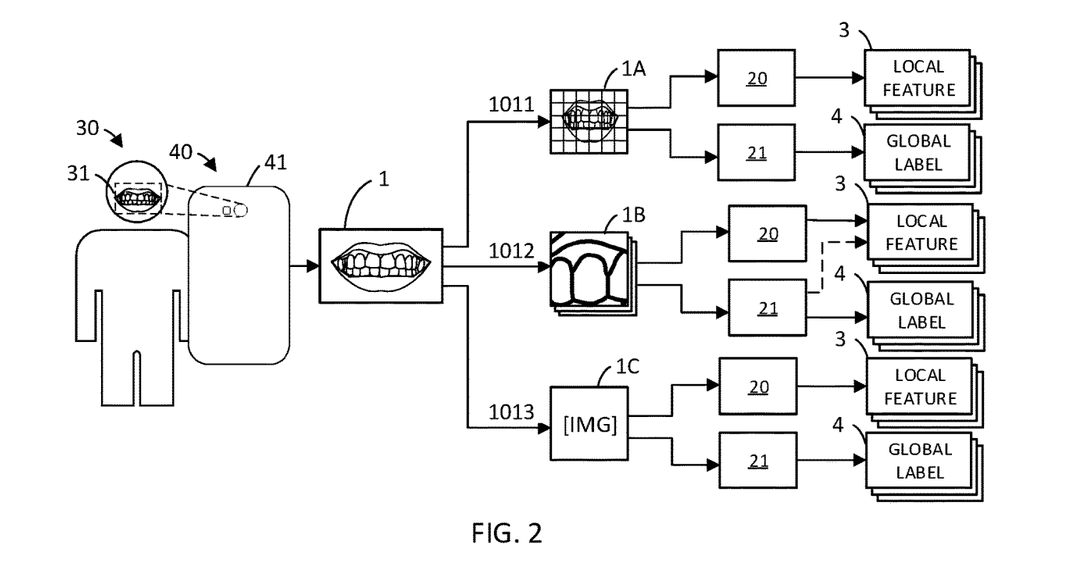
FIG. 2 shows a flow diagram of extracting image derivatives from a digital image and further processing the image derivatives in accordance with a possible implementation form of the first aspect.

FIG. 2 shows a flow diagram of extracting image derivatives from a digital image 1 and further processing the image derivatives in accordance with the present disclosure. In this implementation, steps and features that are the same or similar to corresponding steps and features previously described or shown herein are denoted by the same reference numeral as previously used for simplicity.

As shown in the figure, the method can further comprise extracting at least one image derivative from the digital image 1 obtained using the mobile device 40.

In a possible embodiment the at least one digital image 1 can be processed 1011 by scaling the at least one digital image 1 to optimal dimensions in order to generate at least one scaled image 1A.

In a possible embodiment the at least one digital image 1 can be (further) processed 1012 to extract at least one image patch 1B, each image patch 1B comprising visual information of at least one tooth and its surrounding region within the oral cavity 31. In a possible embodiment a Mask R-CNN model is used for bounding box object detection of the at least one image patch 1B.

In a possible embodiment the at least one digital image 1 can be (further) processed 1013 to extract at least one image vector 1C, each image vector 1C representing the digital image in a reduced vector space, thereby extracting core information and excluding clutter information. In a possible embodiment an unsupervised GAN-based dimensionality reduction is used for extracting the at least one image vector 1C, by sending digital images 1 through an ACGAN model trained on a set of non-annotated (intraoral) images.

In a related embodiment, after extracting at least one image derivative from the digital image 1, the steps of processing the at least one digital image 1 using a statistical algorithm as described above in relation to FIG. 1 may (further) comprise feeding the at least one image derivative 1A, 1B, and/or 1C to a version of the statistical algorithm optimized for the respective image derivative input.

In a possible embodiment, as also illustrated in FIG. 2 with a dashed line, any classification resulting from feeding the at least one image patch 1B to a statistical image recognition algorithm 21 optimized for image patch input can correspond either or both of a global classification label 4 and a local visual feature 3 linked to the respective at least one tooth and its surrounding region within the user's oral cavity 31.

Figure 3:
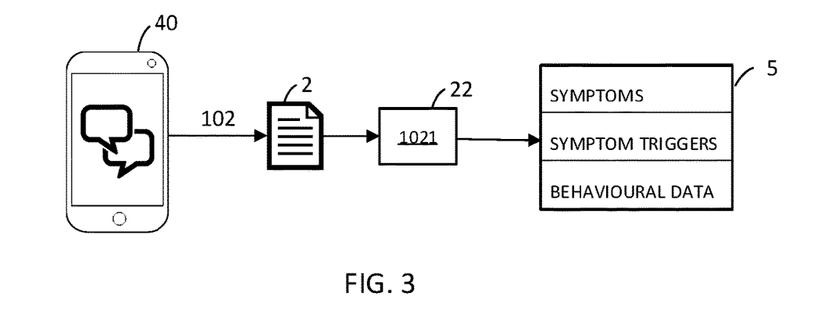
FIG. 3 shows a flow diagram of processing non-image data to extract a structured database of non-image signals in accordance with a possible implementation form of the first aspect.

FIG. 3 shows a flow diagram of processing non-image data 2 to extract a structured database of non-image signals 5 in accordance with the present disclosure, whereby steps and features that are the same or similar to corresponding steps and features previously described or shown herein are denoted by the same reference numeral as previously used for simplicity.

In this embodiment, as illustrated, the non-image data 2 obtained from the mobile device 40 (e.g. in the form of responses to a sequence of questions presented in a chat dialogue) is processed 1021 using a syntax analysis algorithm 22 to extract a structured database of non-image signals 5. In possible embodiments, the extracted non-image signals 5 may comprise at least one of "Sharp", "Pulsatile", "Burning sensation", "Itching", "Tingling", "Radiating", "Stabbing", "Penetrating", "Acute", "Spontaneous", "Periodic", "Constantly", "Provoked", "Swelling", "Growth of tissue",
"Abnormal taste", "Bad breath", "Irregular surface", "Pedunculated", "Redness", "Bleeding spot", "Firm", "Soft", "Compressible", "Pain when biting", "Plaque", "Pain when swallowing", "Sore throat", "Sore gums", "Bleeding gums", "Recession of the gums", "Touch sensitive", or "Loose tooth".

In further possible embodiments, the extracted non-image signals 5 may indicate at least one of:
- symptoms or signs of health regarding intraoral colors, surface structures, contours, wounds, texture, general health, taste in mouth, breath, saliva, healing process, pain;
- symptom triggers related to touch or icing, biting down, movement of tongue or jaw; or
- behavioral data regarding oral habits, general health, medicine intake, comorbidities of periodontitis, history of trauma, history of oral procedures, pregnancy, or tobacco usage.

Figure 4:
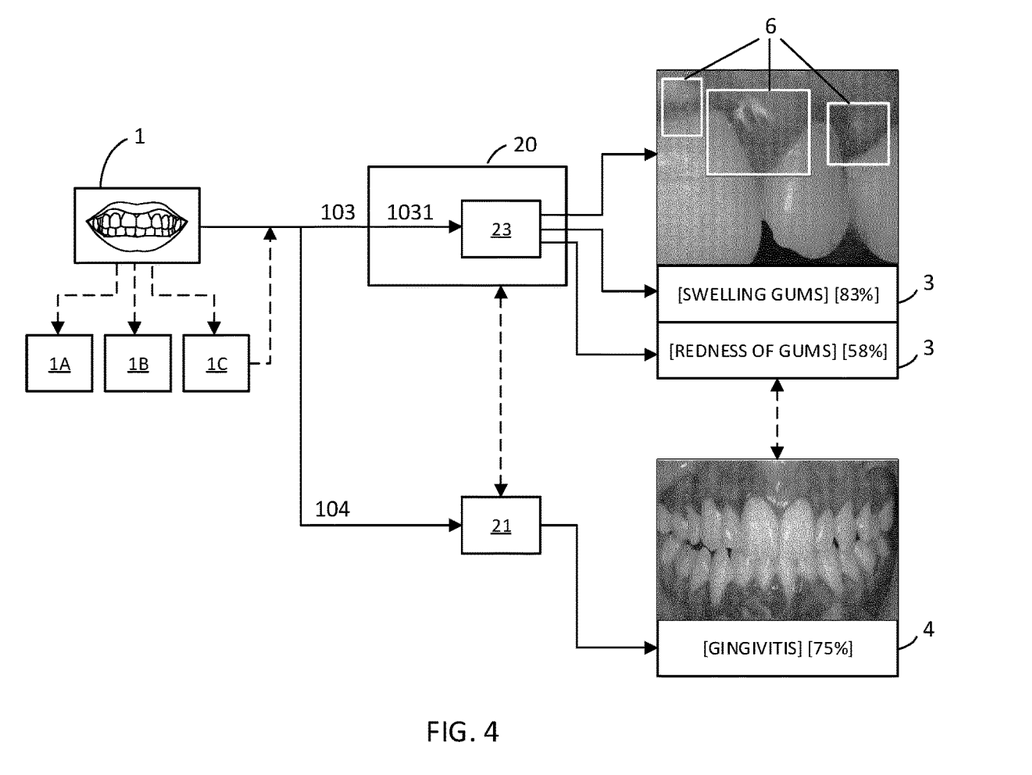
FIG. 4 shows a flow diagram of feeding a digital image or its image derivatives to a classification algorithm as well as an image recognition algorithm in accordance with a possible implementation form of the first aspect.

FIG. 4 shows a flow diagram of feeding a digital image 1 or its image derivatives 1A, 1B, 1C to a classification algorithm 23 as well as an image recognition algorithm 21 in accordance with the present disclosure, whereby steps and features that are the same or similar to corresponding steps and features previously described or shown herein are denoted by the same reference numeral as previously used for simplicity.

In this embodiment the at least one digital image 1 or at least one of its image derivatives 1A, 1B, and/or 1C is fed 1031 to at least one classification algorithm 23 arranged to predict each of the at least one local visual feature 3 and the respective likelihood of the local visual feature 3 independently. The classification algorithm 23 may correspond to any of the statistical object detection algorithms described above in relation to FIG. 1.

In a possible embodiment the classification algorithm 23 is arranged to predict one local visual feature 3.

In a further possible embodiment, the classification algorithm 23 comprises (at least) one multi-label classification algorithm, (each) arranged to predict multiple local visual feature 3 independently from each other; wherein "multi-label" refers to the classification algorithm being arranged so that the labels (local visual features 3) are not mutually exclusive; and wherein "independently" refers to the distribution in the data and the likelihood of co-occurrence of labels (local visual features 3).

In a further possible embodiment, the classification algorithm 23 comprises individual binary algorithms optimized to predict each of the at least one local visual feature 3 respectively, and independently from each other.

In possible embodiments, as described above in relation to FIG. 1, the classification algorithm 23 (or any of its components) is further arranged to predict, for any or each local visual feature 3, at least one local reference 6 indicating a location corresponding to the respective local visual feature 3 on the digital image 1 or any of its image derivatives 1A, 1B, and/or 1C. In a possible embodiment the local reference 6 may comprise a boundary box, and/or an object mask, depending on the model used.

Figure 5:
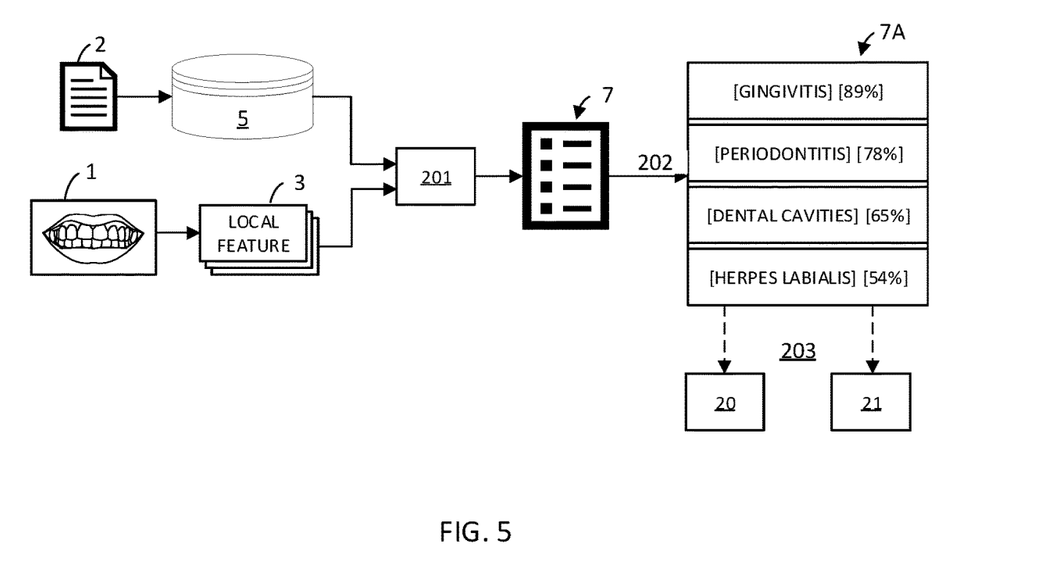
FIG. 5 shows a flow diagram of processing non-image data and local visual feature(s) to extract a set of priority classification labels in accordance with a possible implementation form of the first aspect.

FIG. 5 shows a flow diagram of processing non-image data 2 and local visual feature(s) 3 to extract a set of priority classification labels 7 in accordance with the present disclosure, whereby steps and features that are the same or similar to corresponding steps and features previously described or shown herein are denoted by the same reference numeral as previously used for simplicity.

As illustrated, the non-image data 2 (or its derivative database of non-image signals 5), and the extracted at least one local visual feature 3 is processed 201 using either a statistical or a non-statistical algorithm. The algorithm is arranged to extract a set of priority classification labels 7 corresponding to a predefined number of prioritized medical findings of the user's oral cavity 31, and relative likelihoods of the priority classification labels 7 based on predefined conditions. The priority classification labels in this embodiment refer to a sub-group of approximately 115 global classification labels from a group of approximately 7000 possibly identifiable global classification labels. In a possible embodiment the non-image data 2 (or its derivative database of non-image signals 5), and the at least one local visual feature 3 is processed using filtered queries on a reference database, wherein the reference database may comprise a multi-dimensional set of conditionals, such as age, gender, body structure, various symptom types, and various signs of health, branching into a plurality of dental concepts.

In a next step 202, the set of priority classification labels 7 is arranged into a subset of priority classification labels 7A, wherein the subset comprises the priority classification labels with the highest associated relative likelihoods. In a possible example the subset of priority classification labels 7A comprises two to five priority classification labels 7 such as "gingivitis", "periodontitis", "dental cavities", or "herpes labialis" and their associated likelihood values. In a possible next step 202 the subset of priority classification labels 7A is used as further input for at least one of the statistical object detection algorithm 20 or the statistical image recognition algorithm 21 to enhance the predictability of the at least one local visual feature 3 or the at least one global classification label 4.

Figure 6:
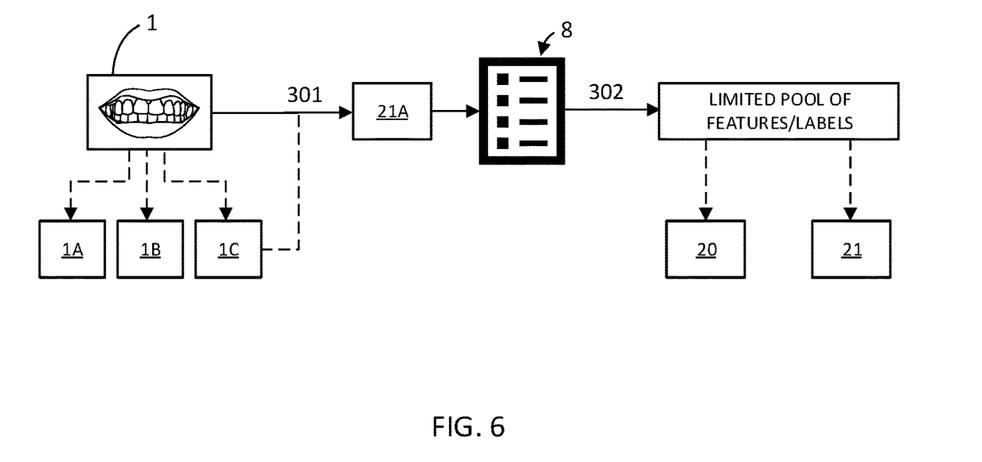
FIG. 6 shows a flow diagram of processing a digital image or its image derivatives to predict a set of pre-classification labels in accordance with a possible implementation form of the first aspect.

In a possible embodiment illustrated in FIG. 6, the at least one digital image 1 or at least one of its derivative scaled image 1A, image patch 1B or image vector 1C is processed 301 using a second statistical image recognition algorithm 21A arranged to predict a set of pre-classification labels 8. The set of pre-classification labels 8 comprises global classification labels corresponding to the most likely possible medical findings of the user's oral cavity 31. This process is primarily explorative, and the main purpose is to identify the labels that are most likely to be extracted in subsequent processing steps.

The second statistical image recognition algorithm 21A may correspond to any of the statistical image recognition algorithms described above in relation to FIG. 1. In a possible embodiment the second statistical image recognition algorithm 21A uses a VGG architecture. In a further possible embodiment, the second statistical image recognition algorithm 21A uses a VGG16 architecture.

In a possible next step 302 the set of pre-classification labels 8 can thus be used as input condition for at least one of the statistical object detection algorithm 20 or the statistical image recognition algorithm 21 to limit the possible result pool of either or both of the algorithms.

Figure 7:
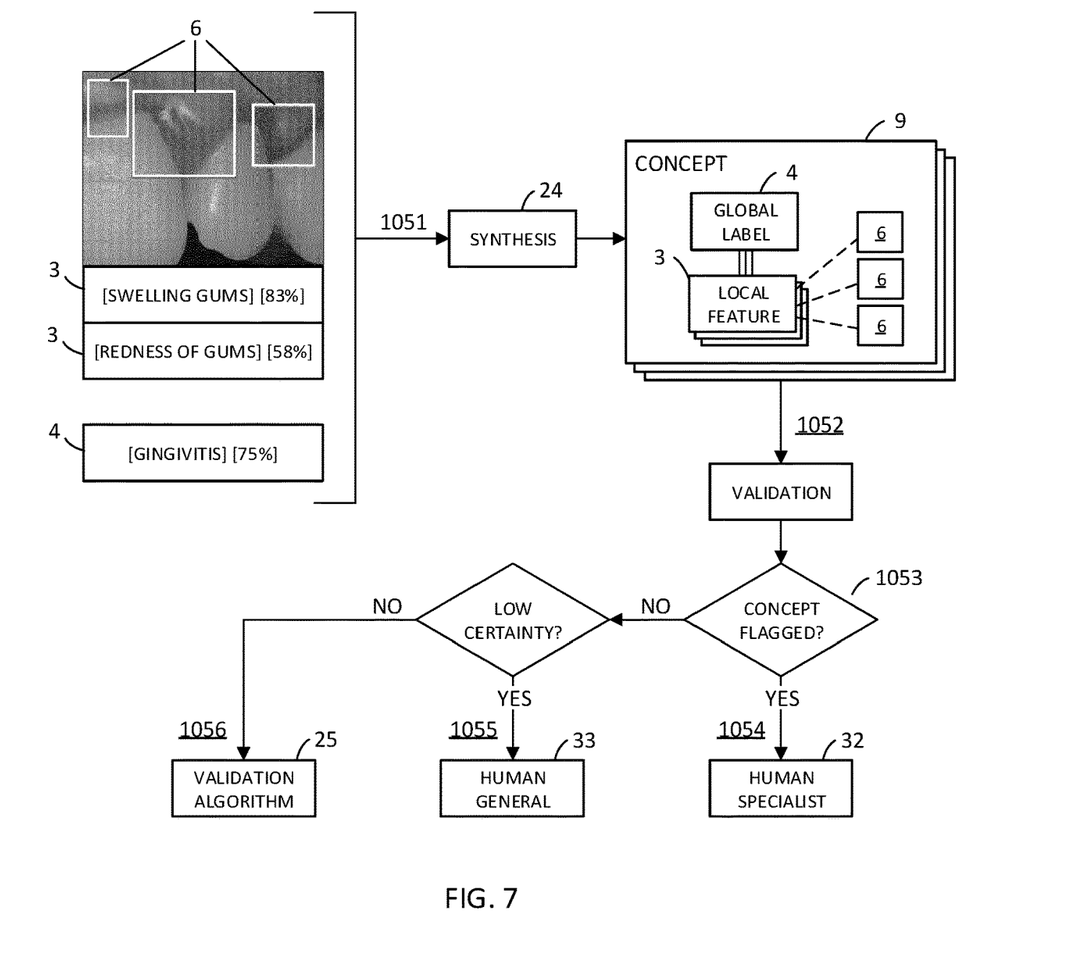
FIG. 7 shows a flow diagram of using a synthesizing algorithm arranged to map local visual features to global classification labels and to determine a set of concepts and validating the set of concepts either automatically or by a human dental reviewer in accordance with a possible implementation form of the first aspect.

FIG. 7 illustrates a further possible embodiment wherein a synthesizing algorithm 24 is arranged to map local visual features 3 to global classification labels 4 and to determine a set of concepts 9, which are then validated either automatically or by a human dental reviewer in accordance with the present disclosure.

Accordingly, in a first step 1051 the likelihood of the at least one local visual feature 3 (and its corresponding at least one local reference 6 as described above), and the likelihood of the at least one global classification label 4 is fed to a synthesizing algorithm 24 arranged to map local visual features 3 to global classification labels 4. The synthesizing algorithm 24 is thus trained to determine a set of concepts 9, each concept 9 comprising at least one global classification label 4 and any number of related local visual feature(s) 3 and their (optional) local references 6.

In a next, optional step 1052 the set of concepts 9 is validated either automatically or by a human dental reviewer 32,33 based on medical certainty. In an embodiment the human dental reviewer 32,33 may be a dental professional (e.g. dentist, dental hygienist, dental therapist, dental nurse, dental technician), a medical practitioner, or another health professional.

In a possible embodiment the medical certainty is determined based on predefined threshold values for the likelihoods of the global classification labels 4 and related local visual features 3 comprised in each concept 9, as well as predefined threshold values for validity scores associated with each statistical algorithm used for predicting the likelihoods of the global classification labels 4 and related local visual features 3 comprised in each concept 9.

In an embodiment the list of concepts 9 is further processed 1053 using a specialist reference database, wherein any concept 9 is flagged that comprises a global classification label 4 or a related local visual feature 3 that is defined in the specialist reference database as any one of
extraordinarily rare,
extraordinarily malignant, or
transcending into the domain of general health.

Once the flagging is complete, the concepts are routed according to the following sequence of conditions:
1) if a concept 9 is flagged, it is forwarded 1054 to a human specialist dental reviewer 32 for validation;
2) if medical certainty of a concept 9 is lower than a predefined medical certainty threshold but the concept 9 is not flagged, it is forwarded 1055 to a human general dental reviewer 33 for validation; and
3) the remaining list of concepts 9 is validated 1056 using a validation algorithm 25 arranged for automatic concept 9 validation based on a predefined set of validation rules.

In an embodiment the role of human general dental reviewer 33 may be filled by the same person as the human specialist dental reviewer 32.

Figure 8:
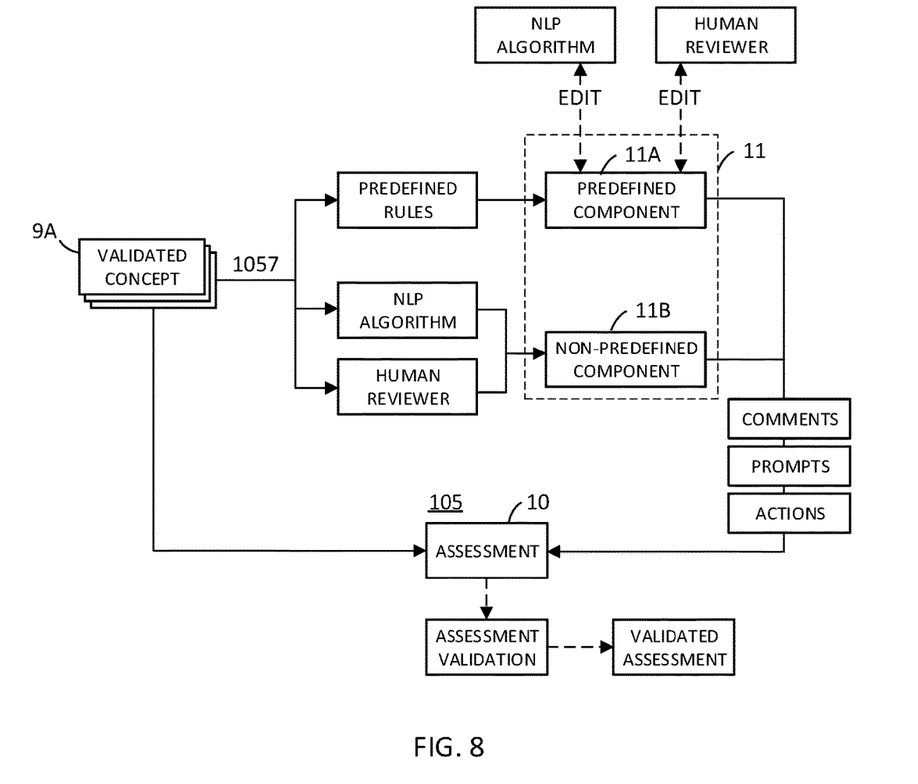
FIG. 8 shows a flow diagram of processing a list of validated concepts to determine additional components for the assessment in accordance with a possible implementation form of the first aspect.

FIG. 8 illustrates a further possible embodiment wherein the list of validated concepts 9A is processed 1057 to determine additional components 11 for the assessment 10. In an embodiment the additional components 11 comprise comments or prompts and possible or typical actions to take in case of an identified concept 9, global classification label 4 or related local visual feature 3.

In a possible embodiment the list of validated concepts 9A is processed using a parsing algorithm arranged to parse through each validated concept 9A and extract comments and actions from database comprising predefined comments or prompts and possible/typical actions to take given a noted issue. This database may be based on research-based dental knowledge on typical visual signs, actions, and suggestions on behavioral adjustments related to concepts combined with personalized documentation for the user 30.

In a possible embodiment determining the additional components 11 comprises determining a predefined component 11A from multiple possible predefined components 11A automatically, based on predefined rules. The predefined component 11A may be further edited manually by a human reviewer, or automatically using a statistical natural language processing (NLP) algorithm. In a further possible embodiment determining the additional components 11 (further) comprises determining a non-predefined component 11B. The non-predefined component 11B may be determined manually (by a human reviewer), and/or automatically using an NLP algorithm.

In the final step 105 the assessment 10 of the oral health of the user 30 may then be determined based on the validated list of concepts 9 and the additional components 11.

In a further optional step, the full assessment is further validated either automatically or by the general or specialist dental reviewer based on medical certainty and the presence of any flagged concept, similarly as described above with respect to concept validation.

In an embodiment the validated full assessment is further filtered before presented to the user 30 using a filter database to mask, remove or replace any concept defined as sensitive in the filter database (such as "malignant tumor").

Figure 9:
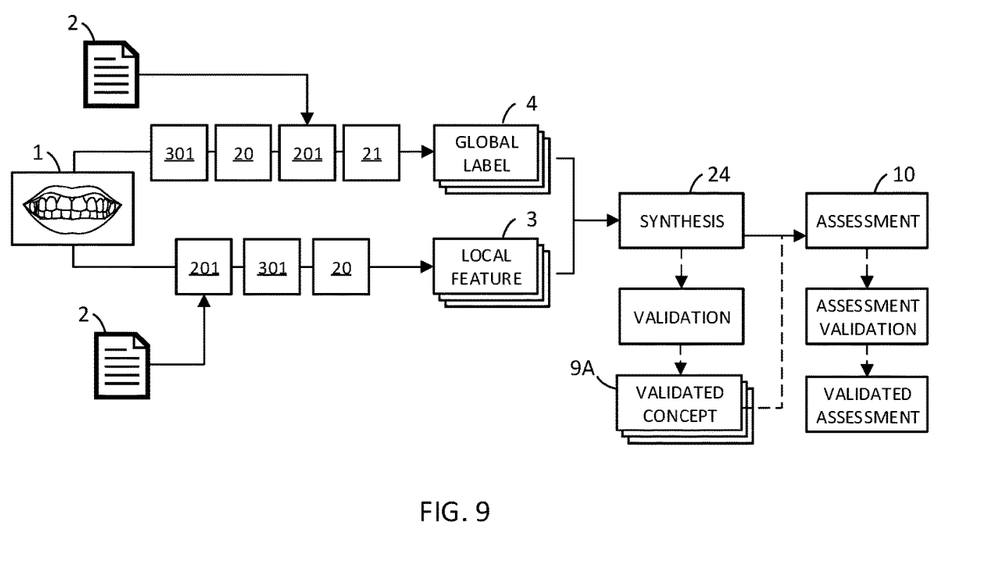
FIG. 9 shows a flow diagram of a parallel pipeline arrangement for determining an assessment of oral health of a user in accordance with a possible implementation form of the first aspect.

FIG. 9 shows a flow diagram of an exemplary "parallel pipeline" arrangement for determining an assessment 10 of oral health of a user 30 in accordance with the present disclosure, whereby steps and features that are the same or similar to corresponding steps and features previously described or shown herein are denoted by the same reference numeral as previously used for simplicity.

In this exemplary "parallel pipeline" arrangement two parallel sequences of algorithms are arranged to determine at least one local visual feature 3 and at least one global classification label 4 based on at least one digital image 1 (and/or its image derivatives 1A,1B,1C) and non-image data 2 (or its derivative database of non-image signals 5).

On one "side" of the pipeline the at least one digital image 1 is first processed 301 using the second statistical image recognition algorithm 21A arranged to predict a set of pre-classification labels 8. This set of pre-classification labels 8 is then used to limit the possible result pool of the subsequent statistical object detection algorithm 20 (as well as the subsequent image recognition algorithm 21). In a further step the at least one digital image 1 is processed by a statistical object detection algorithm 20, as described above, thereby extracting at least one local visual feature 3, its corresponding likelihood and optional local reference 6. In a further step the extracted local visual feature(s) 3 and corresponding likelihood(s) and optional local reference(s) 6 and the additionally obtained non-image data (and/or its derivative database of non-image signals 5) is processed 201 using a statistical or non-statistical algorithm to extract a set of priority classification labels 7, and from this set a subset of priority classification labels 7A, which is then used as further input for the subsequent statistical image recognition algorithm 21 to enhance the predictability of the final extracted at least one global classification label 4.

On the other "side" of the pipeline the at least one digital image 1 (and/or its image derivatives 1A,1B,1C) and additional non-image data 2 (and/or its derivative database of non-image signals 5) is processed 201 using a statistical or non-statistical algorithm to extract a set of priority classification labels 7, and from this set a subset of priority classification labels 7A. Using a subsequently arranged second statistical image recognition algorithm 21A the at least one digital image 1 (and/or its image derivatives 1A,1B,1C) is further processed 301 to extract a set of pre-classification labels 8. These extracted pre-classification labels 8 and priority classification labels 7A are then used as input for the subsequently arranged statistical object detection algorithm 20 to enhance the predictability of the final extracted at least one local visual feature 3.

Once the global classification label(s) 4 and local visual feature(s) 3 are determined, they are processed using an above described synthesizing algorithm 24 to determine a set of concepts 9, which can then be validated as described above in detail. The (validated) concepts 9 (9A) can then be used to determine the final assessment 10, using optionally further determined predefined components 11A and/or non-predefined components 11B. The assessment 10 can then be further validated and filtered, as described above.

Figure 10:
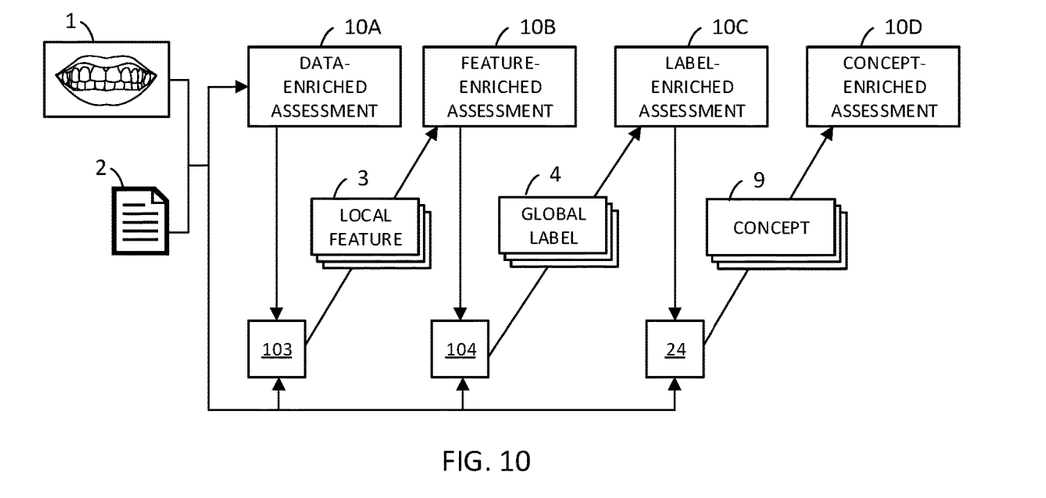
FIG. 10 shows a flow diagram of a zig-zag arrangement for determining an assessment of oral health of a user in accordance with a possible implementation form of the first aspect.

FIG. 10 shows a flow diagram of an exemplary "zig-zag" arrangement for determining an assessment 10 of oral health of a user 30 in accordance with the present disclosure, whereby steps and features that are the same or similar to corresponding steps and features previously described or shown herein are denoted by the same reference numeral as previously used for simplicity. This arrangement is advantageous because of its flexibility and scalability, as it allows for easier addition of further components/layers. In this arrangement the at least one digital image 1 (and/or its image derivatives 1A,1B,1C) and additional non-image data (and/or its derivative database of non-image signals 5) is processed first to determine a preliminary, data-enriched assessment 10A.

This data-enriched assessment 10A is then further enhanced by at least one local visual feature 3, extracted 103 using a statistical object detection algorithm 20 as described above, thereby resulting in a feature-enriched assessment 10B. This feature-enriched assessment 10B is then further enhanced by at least one global classification label 4, extracted 104 using a statistical image recognition algorithm 21 as described above, thereby resulting in a label-enriched assessment 10C.

This label-enriched assessment 10C is then further enhanced by at least one concept 9, determined using a synthesizing algorithm 24 as described above, thereby resulting in a concept-enriched assessment 10D. This concept-enriched assessment 10D can then be further validated and/or filtered, as described above, and presented to the user 30 on the mobile device 40.

FIG. 11 is a block diagram of a system for assessing oral health of a user in accordance with the present disclosure. The illustrated mobile device 40 comprises a camera 41 for obtaining at least one digital image 1 of the oral cavity of a user 30, a machine-readable storage medium 43.

The method described above for assessing oral health may at least partly be implemented as a computer program product 42 encoded on the machine-readable storage medium 43. The computer program product 42 may in effect be realized in the form of an application software ("app") which may be executed on the mobile device 40 by one or more processors 44 which may load the application software on a memory 45 and result in providing a graphical user interface on a display 48 of the mobile device 40. In an embodiment the display 48 may comprise a touchscreen input interface 47 through which the user 30 may interact with the application software on the mobile device 40.

The mobile device 40 may further comprise an integrated or external communications interface 46 for connecting to other mobile devices or a computer network. For example, the communications interface 46 can include Wi-Fi enabling circuitry that permits wireless communication according to one of the 802.11 standards or a private network. Other wired or wireless protocol standards, such as Bluetooth, can be used in addition or instead.

The mobile device 40 may further comprise an internal bus 49 arranged to provide a data transfer path for transferring data to, from, or between the mentioned components of the mobile device 40.

FIG. 12 is a diagrammatic representation of a wireless system in accordance with the present disclosure.

The mobile device 40 can communicatively be connected to a network of computer nodes using an integrated or external communications interface 46 as shown in FIG. 11, e.g. for transmitting image data and/or non-image data from the mobile device 40 to a computer node and/or for receiving data from a computer node. The figure shows a diagrammatic representation of an exemplary wireless network, such as a cellular telephone network, the internet, or a cloud-based network, comprising the mobile device 40, a remote server 50, and a dental professional's workstation 51. Image data and/or non-image data may be transmitted from the mobile device 40 to the remote server 50 and/or the dental professional's workstation 51 for remote assessment, processing, and/or storage of the data. The transmission of data may be synchronous, asynchronous, or a mixture of synchronous and asynchronous data transmission.

The various aspects and implementations have been described in conjunction with various embodiments herein. However, other variations to the disclosed embodiments can be understood and effected by those skilled in the art in practicing the claimed subject-matter, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems.

The reference signs used in the claims shall not be construed as limiting the scope.

The invention claimed is:

1. A computer-implemented method for assessing oral health of a user of a mobile device to determine whether the user is a candidate for an oral treatment, the method comprising:
    obtaining (101) at least one digital image (1) of the user's (30) oral cavity (31) using a camera (41) of the mobile device (40);
    obtaining (102) non-image data (2) associated with the user (30) using the mobile device (40), the non-image data (2) comprising anamnestic information about the user;
    processing (103) the at least one digital image (1) using a statistical object detection algorithm (20) executed on a processor of the mobile device (40) or a processor of a remote server (50) to calculate the likelihood of at least one local visual feature (3) corresponding to a medical finding related to a sub-region of the user's oral cavity (31);
    processing (104) the at least one digital image (1) using a statistical image recognition algorithm (21) executed on a processor of the mobile device (40) or a processor of a remote server (50) to calculate the likelihood of at least one global classification label (4) corresponding to a medical finding related to the user's oral cavity (31);
    processing (201) the non-image data (2) and the at least one local visual feature (3) using a statistical or non-statistical algorithm executed on a processor of the mobile device (40) or a processor of a remote server (50) to extract a set of priority classification labels (7) corresponding to a predefined number of prioritized medical findings of the user's oral cavity (31), and relative likelihoods of the priority classification labels (7) based on predefined conditions;
    arranging (202) the set of priority classification labels (7) into a subset of priority classification labels (7A) of highest relative likelihoods;
    using (203) the subset of priority classification labels (7A) as further input for at least one of the statistical object detection algorithm (20) or the statistical image recognition algorithm (21) to enhance the predictability of the at least one local visual feature (3) or the at least one global classification label (4);
    determining (105) an assessment (10) of the oral health of the user (30) using a processor of the mobile device (40) or a processor of a remote server (50) by feeding (1051) the likelihood of the at least one local visual feature (3) and the likelihood of the at least one global classification label (4) to a synthesizing algorithm (24) arranged to map local visual features (3) to global classification labels (4) and to determine a set of concepts (9), each concept (9) comprising at least one global classification label (4) and any number of related local visual features (3); and
    validating (1052) the set of concepts (9) either automatically or by a human dental reviewer (32,33) based on medical certainty, wherein the medical certainty is determined based on at least one of:
        predefined threshold values for the likelihoods of the global classification labels (4) and related local visual features (3) comprised in each concept; and
        predefined threshold values for validity scores associated with each statistical algorithm used for predicting the likelihoods.

2. A method according to claim 1, wherein the at least one digital image (1) is at least one of an intraoral or extraoral high resolution color photograph, preferably in the RGB or RGBA color space; and wherein the method further comprises extracting at least one image derivative (1A,1B,1C) from the digital image (1) by at least one of:
    processing (1011) the at least one digital image (1) to generate at least one scaled image (1A) by scaling the at least one digital image (1) to optimal dimensions;
    processing (1012) the at least one digital image (1) to extract at least one image patch (1B), each image patch (1B) comprising visual information of at least one tooth and its surrounding region within the oral cavity (31); and
    processing (1013) the at least one digital image (1) to extract at least one image vector (1C), each image vector (1C) representing the digital image (1) in a reduced vector space; wherein processing the at least one digital image (1) using a statistical algorithm comprises feeding the at least one image derivative (1A,1B,1C) to a version of the statistical algorithm optimized for the respective image derivative (1A,1B,1C) input; and wherein
    any classification resulting from feeding the at least one image patch (1B) to a statistical image recognition algorithm (21) optimized for image patch input can correspond to at least one of a global classification label (4), or a local visual feature (3) linked to the respective at least one tooth and its surrounding region within the user's oral cavity (31).

3. A method according to claim 2, wherein processing (103) the at least one digital image (1) using a statistical object detection algorithm (20) arranged to calculate the likelihood of at least one local visual feature (3) comprises:
    feeding (1031) the at least one digital image (1) or at least one of its image derivatives (1A,1B,1C) to at least one classification algorithm (23) arranged to predict each of the at least one local visual feature (3) independently, wherein the at least one classification algorithm (23) is arranged to further predict:
    the likelihood of the respective local visual feature (3), and
    at least one local reference (6) indicating a location corresponding to the respective local visual feature (3) on the digital image (1) or any of its image derivatives (1A,1B,1C).

4. A method according to claim 2, further comprising:
    processing (301) the at least one digital image (1) or at least one of its image derivatives (1A,1B,1C) using a second statistical image recognition algorithm (21A) arranged to predict a set of pre-classification labels (8) corresponding to the most likely possible medical findings of the user's oral cavity (31); and
    using (302) the set of pre-classification labels (8) as input condition for at least one of the statistical object detection algorithm (20) or the statistical image recognition algorithm (21) to limit the possible result pool of either or both of the algorithms.

5. A method according to claim 1, wherein the non-image data (2) comprises self-reported user input obtained using the mobile device in the form of at least one of a checklist, a slider bar, or free text; and wherein the method further comprises:
processing (1021) the non-image data (2) using a syntax analysis algorithm (22) to extract a structured database of non-image signals (5), the non-image signals (5) indicating at least one of
symptoms or signs of health regarding intraoral colors, surface structures, contours, wounds, texture, general health, taste in mouth, breath, saliva, healing process, pain;
symptom triggers related to touch or icing, biting down, movement of tongue or jaw; or
behavioral data regarding oral habits, general health, medicine intake, comorbidities of periodontitis, history of trauma, history of oral procedures, pregnancy, or tobacco usage.

6. A method according to claim 1, wherein the statistical object detection algorithm (20) uses a neural network model, more preferably a convolutional neural network model.

7. A method according to claim 1, wherein at least one of
the at least one local visual feature (3) is used as further input for the statistical image recognition algorithm (21) to enhance the predictability of the at least one global classification label (4); or
the at least one global classification label (4) is used as further input for the statistical object detection algorithm (20) to enhance the predictability of the at least one local visual feature (3).

8. A method according to claim 1, wherein the at least one global classification label (4) corresponds to at least one of "gingivitis", "periodontitis", "dental cavities", or "herpes labialis".

9. A method according to claim 8, wherein one or more predefined local visual feature (3) may increase the likelihood of at least one global classification label (4), such as:
"swelling gums", "bleeding gums", "redness of gums", "dental plaque" may increase the likelihood of "gingivitis";
"exposure of root", "abrasion of tooth", "staining of tooth", "recession of gums" may increase the likelihood of "periodontitis";
"white spot lesion", "brown/black discoloration of tooth", "enamel breakdown", "shade on enamel", "dental plaque" may increase the likelihood of "dental cavities";
"inflamed papules and vesicles", "fluid-filled blister", "local redness of lip", "open ulcer" may increase the likelihood of "herpes labialis"; and
"light coral pink gums", "stippled surface gums", "tightly fitting gumline on tooth" may increase the likelihood of "healthy gums".

10. A method according to claim 1, further comprising:
processing (1053) the set of concepts (9) using a specialist reference database and flagging any concept (9) comprising a classification label or a related local visual feature (3) that is defined in the specialist reference database as any one of
extraordinarily rare,
extraordinarily malignant, or
transcending into the domain of general health; and
if a concept (9) is flagged, forwarding (1054) it to a human specialist dental reviewer (32) for validation;
if medical certainty of a concept (9) is lower than a predefined medical certainty threshold but the concept (9) is not flagged, forwarding (1055) it to a human general dental reviewer (33) for validation; and
validating the remaining set of concepts (9) using (1056) a validation algorithm (25) arranged for automatic concept (9) validation based on a predefined set of validation rules.

11. A method according to claim 10, further comprising:
processing (1057) the list of validated concepts (9A) to determine additional components (11) for the assessment (10), the additional components (11) comprising comments or prompts and possible or typical actions to take in case of an identified concept (9), global classification label (4) or related local visual feature (3), wherein determining the additional components (11) comprises at least one of:
determining a predefined component (11A) from multiple possible predefined components (11A) automatically based on predefined rules,
editing a predefined component (11A) manually by a human reviewer,
editing a predefined component (11A) automatically using a statistical natural language processing (NLP) algorithm,
determining a non-predefined component (11B) manually by a human reviewer, and
determining a non-predefined component (11B) automatically using a statistical natural language processing (NLP) algorithm; and
determining (105) an assessment (10) of the oral health of the user (30) based on the list of validated concepts (9A) and the additional components (11).

12. A computer program product (42), encoded on a non-transitory computer-readable storage medium (43), operable to cause a processor (44) of a mobile device (40) or a processor of a remote server (50) to perform operations according to the method of claim 1.

13. A system for assessing oral health of a user, the system comprising:
a mobile device (40) comprising a camera (41) for obtaining at least one digital image (1) of the user's oral cavity (31);
a machine-readable storage medium (43) comprising a program product (42);
a remote server (50) in data connection with the mobile device (40); and
one or more processors (44) operable to execute the program product (42) and perform operations according to the method of claim 1.

* * * * *